(12) United States Patent
Peppou et al.

(10) Patent No.: US 9,980,672 B2
(45) Date of Patent: May 29, 2018

(54) SINGLE-CHAMBERED SWEAT RATE MONITORING SENSOR

(71) Applicant: Empire Technology Development LLC, Wilmington, DE (US)

(72) Inventors: George Charles Peppou, Rosebery (AU); Michael Keoni Manion, Seattle, WA (US); Benjamin William Millar, Rosebery (AU)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 390 days.

(21) Appl. No.: 14/801,702

(22) Filed: Jul. 16, 2015

(65) Prior Publication Data

US 2017/0014067 A1    Jan. 19, 2017

(51) Int. Cl.
*A61B 5/05* (2006.01)
*A61B 5/00* (2006.01)
*A61B 10/00* (2006.01)

(52) U.S. Cl.
CPC ........ *A61B 5/4266* (2013.01); *A61B 10/0064* (2013.01); *A61B 5/0022* (2013.01); *A61B 5/4875* (2013.01); *A61B 5/681* (2013.01); *A61B 5/6831* (2013.01); *A61B 5/6833* (2013.01); *A61B 5/7475* (2013.01)

(58) Field of Classification Search
CPC .......................... A61B 10/0064; A61B 5/6833
See application file for complete search history.

(56) References Cited

U.S. PATENT DOCUMENTS

| | | | |
|---|---|---|---|
| 4,962,662 A | 10/1990 | Berger | |
| 5,050,604 A | 9/1991 | Reshef et al. | |
| 5,131,390 A | 7/1992 | Sakaguchi et al. | |
| 5,224,510 A | 7/1993 | Pericles | |

(Continued)

FOREIGN PATENT DOCUMENTS

| | | |
|---|---|---|
| CN | 103054556 A | 4/2013 |
| JP | H07209056 A | 8/1995 |
| WO | 2013179240 A1 | 12/2013 |

OTHER PUBLICATIONS

"Body surface area," Wikipedia, accessed at http://web.archive.org/web/20150326205950/http://en.wikipedia.org/wiki/Body_surface_area, last modified on Feb. 19, 2015, pp. 1-5.

(Continued)

*Primary Examiner* — Puya Agahi

(57) ABSTRACT

Technologies are generally described to monitor a sweat rate of an area of a skin. A hydration status of a human or non-human entity is monitored based on the sweat rate. The sweat rate is monitored when the sweat rate monitor is detected as sealed against the surface of the skin. The sweat rate monitor is attached to the surface of the skin with an adhesive, or a tape among other schemes to hold the sweat rate monitor in place during a measurement. The sweat rate monitor includes a container to capture an initial amount of sweat that comes out of the surface of the skin. When, the container is detected as filled with the initial amount of sweat, a pump of the sweat rate monitor is actuated to compress the container. The container is compressed to force a volume of the initial amount of sweat in the container out of an ejection port of the sweat rate monitor.

8 Claims, 11 Drawing Sheets

(56) References Cited

U.S. PATENT DOCUMENTS

| | | | |
|---|---|---|---|
| 5,417,235 | A | 5/1995 | Wise et al. |
| 6,076,522 | A | 6/2000 | Dwivedi et al. |
| 6,095,175 | A | 8/2000 | Miller et al. |
| 6,206,022 | B1 | 3/2001 | Tsai et al. |
| 6,269,265 | B1 | 7/2001 | Anderson |
| 6,349,740 | B1 | 2/2002 | Cho et al. |
| 6,539,968 | B1 | 4/2003 | White et al. |
| 7,124,773 | B2 | 10/2006 | Midtgard et al. |
| 7,666,687 | B2 | 2/2010 | Webster et al. |
| 7,918,238 | B2 | 4/2011 | Tanaka et al. |
| 8,650,946 | B1 | 2/2014 | Feller |
| 8,789,556 | B2 | 7/2014 | Yasuda et al. |
| 2004/0107996 | A1 | 6/2004 | Crocker et al. |
| 2004/0202548 | A1 | 10/2004 | Dai et al. |
| 2005/0160833 | A1 | 7/2005 | Gerhardt et al. |
| 2005/0287043 | A1 | 12/2005 | Stromereder et al. |
| 2007/0027383 | A1* | 2/2007 | Peyser ............... A61B 5/14521 600/347 |
| 2007/0089789 | A1 | 4/2007 | Mudd et al. |
| 2009/0054746 | A1 | 2/2009 | Cho |
| 2009/0105605 | A1 | 4/2009 | Abreu |
| 2010/0063372 | A1 | 3/2010 | Potts et al. |
| 2010/0132485 | A1 | 6/2010 | Erez et al. |
| 2011/0111516 | A1 | 5/2011 | Lee et al. |
| 2012/0090703 | A1 | 4/2012 | Li et al. |
| 2012/0150072 | A1 | 6/2012 | Revol-Cavalier et al. |
| 2013/0129580 | A1 | 5/2013 | Flavin et al. |
| 2013/0253872 | A1 | 9/2013 | Curtis et al. |
| 2013/0303967 | A1 | 11/2013 | Utz et al. |
| 2014/0066867 | A1 | 3/2014 | Locke et al. |
| 2015/0316172 | A1 | 11/2015 | Bustgens |

OTHER PUBLICATIONS

"Perspiration," Wikipedia, accessed at http://web.archive.org/web/20150714104705/https://en.wikipedia.org/wiki/Perspiration, last modified on Jul. 13, 2015 , pp. 5.

Coyle, S., et al., "Textile sensors to measure sweat pH and sweat-rate during exercise," 3rd International Confrence on Pervasive Computing Technologies for Healthcare, pp. 1-6 (Apr. 1-3, 2009).

Dubois, D., and Dubois, E.F, "A formula to estimate the approximate surface area if height and weight be known," Arch Int Med, vol. 17, pp. 863-871 (1916).

Feng, Y., et al., "Passive valves based on hydrophobic microfluidics," Sensors and Actuators A, vol. 108, pp. 138-143 (2003).

International serach report and written opinion for International Application No. PCT/US2016/019305 dated Jun. 30, 2016.

International serach report and written opinion for International Application No. PCT/US2016/037302 dated Sep. 27, 2016.

Klinker, L. E., "Skin-Based Sweat Monitoring Using Radio Frequency Identification Sensors," An honors thesis for the Department of Biomedical Engineering, pp. 1-97 (2012).

Kono, T. , et al., "Wearable Sized Sudorometer and Sweat Measurement," Transactions of Japanese Society for Medical and Biological Engineering, vol. 51, R-139, pp. 1-1 (2013).

Kraning, K.K. and Sturgeon, D., A. , "Measurement of sweating rate with capacitance sensors," Annals of Biomedical Engineering, vol. 11, No. 2, pp. 131-146 (Mar. 1983).

Lemon P. W. and Yarasheski K. E., "Feasibility of sweat collection by whole body washdonw in moderate to high humidity environments," International Journal of Sports Medicine, vol. 6, No. 1, pp. 41-43 (Feb. 1985).

Leng, H., and Lin, Y., et al., "Design and fabrication of a sensor integrated MEMS/NANO-skin system for human physiological response measurement," Proc. SPIE 7647, Sensors and Smart Structures Technologies for Civil, Mechanical, and Aerospace Systems, vol. 7647, pp. 12 (Mar. 31, 2010).

Maughan, R. J., "Impact of mild dehydration on wellness and on exercise performance," European Journal of Clinical Nutrition, vol. 57, Suppl 2, pp. S19-S23 (Dec. 2003).

McClure, J. A., et al., "A Sweat Sensor for Qualitative Measurements," Aerospace Medical Research, vol. 43, No. 11, pp. 1-24 (Nov. 1972).

Sacco, J.J., et al., "The Average Body Surface Area of Adult Cancer Patients in the UK: A Multicentre Retrospective Study," PLoS One, vol. 5, No. 1 : e8933, pp. 1-6 (Jan. 28, 2010).

Salvo, P., et al., "A Wearable Sensor for Measuring Sweat Rate," IEEE Sensors Journal, vol. 10, No. 10, pp. 1557-1558 (Oct. 2010).

Smith, C. J., and Havenith, G., "Body Mapping of Sweating Patterns in Athletes : A Sex Comparison," Medicine and science in sports and exercise, vol. 44, No. 12, pp. 2350-2361 (2012).

Yokota, M., et al., "Transient Sweat Rate Calculation from Humidity Measurements under Clothing," Conference paper, Army Research Inst of Environmental Medicine Natick Ma Biophysics and Biomedical Modeling Div, pp. 1-10 (Jul. 2006).

"Body surface area," Wikipedia, Retrieved from URL: https://web.archive.org/web/20140913182149/http://en.wikipedia.org/wiki/Body_surface_area, on Feb. 3, 2015, Aug. 31, 2014, pp. 1-5.

"Perspiration," Wikipedia, Retrieved from URL: https://web.archive.org/web/20150108195820/http://en.wikipedia.org/wiki/Perspiration, on Jan. 29, 2015, last modified Jan. 8, 2015 , pp. 1-6.

Coyle, S., et al., "Textile sensors to measure sweat pH and sweat-rate during exercise," In: Pervasive Health 2009, pp. 1-6 (Apr. 1-3, 2009).

Kraning, K.K. and Sturgeon, D., A. , "Measurement of sweating rate with capacitance sensors," Annals of Biomedical Engineering, vol. 11, No. 2, pp. 131-146 (1983).

Lemon P. W. and Yarasheski K. E, "Feasibility of sweat collection by whole body washdonw in moderate to high humidity environments," International Journal of Sports Medicine, vol. 6, pp. 41-43 (Feb. 1985).

Leng, H., and Lin, Y., et al., "Design and fabrication of a sensor integrated MEMS/NANO-skin system for human physiological response measurement," Proc. SPIE 7647, Sensors and Smart Structures Technologies for Civil, Mechanical, and Aerospace Systems, vol. 7647, pp. (Mar. 31, 2010).

Maughan, R. J., "Impact of mild dehydration on wellness and on exercise performance," European Journal of Clinical Nutrition, vol. 57, Suppl 2, pp. S19-S23 (2003).

Sacco, J.J., et al., "The Average Body Surface Area of Adult Cancer Patients in the UK: A Multicentre Retrospective Study," PLoS One, vol. 5, No. 1 : e8933, pp. 1-6 ( Jan. 28, 2010).

Smith, C. J., and Havenith, G., "Body Mapping of Sweating Patterns in Athletes : A Sex Comparison," Environmental Ergonomics Research Center, Med Sci Sports Exerc., vol. 44, No. 12, pp. 2350-2361 (Dec. 2012).

* cited by examiner

SINGLE-CHAMBERED SWEAT RATE MONITORING SENSOR

BACKGROUND

Unless otherwise indicated herein, the materials described in this section are not prior art to the claims in this application and are not admitted to be prior art by inclusion in this section.

Maintaining hydration benefits a person's health and athletic performance. A reduction in total body water of 1% to 2% of body mass may impair cognitive performance and physical performance. Serious health risks, including death, may occur when water loss exceeds 7% of body mass. Hydration may be defined as a process of absorbing and retaining water in biological tissues. To measure hydration, one may monitor total body water turnover (TBWT), which is the difference between the amount of water that may be absorbed into a body and the amount of water that leaves the body.

A majority of fluid loss during exercise may be due to perspiration. In order to measure the amount of fluid loss to perspiration, the "wash down method" may be utilized to measure the TBWT. However, the wash down method fails to provide a real-time measurement of perspiration. Other measurement methods, such as fabric sensors, osmotic sensors, evaporation sensors, and optical sensors, suffer from limitations such as, saturation concerns, inaccuracy, portability concerns, and an inability to measure the rate of sweat in real-time.

SUMMARY

The present disclosure generally describes techniques for monitoring a sweat rate of an area of a skin.

In some examples, methods to monitor a sweat rate of an area of a skin are described. An example method may include detecting a sweat rate monitor as sealed against a surface of the skin, detecting the container as filled with the initial sweat, actuating a pump of the sweat rate monitor to compress the container in order to force a volume of the initial sweat in the container out of an ejection port of the sweat rate monitor, and measuring a start time of actuation of the pump and a refill time of the container with an additional sweat to determine the sweat rate. The sweat rate monitor may include a container to capture an initial sweat that comes out of the surface of the skin.

According to some examples, sweat rate monitor modules to monitor a sweat rate of an area of a skin are described. An example sweat rate monitor module may include a container, one or more analog inputs, a support ring, and a processor. The container may be configured to capture an initial sweat that comes out of a surface of the skin. The one or more analog inputs may be attached to the container. The support ring may encapsulate the container. The processor may be configured to detect the container as filled with the initial sweat, actuate a pump attached to the support ring to compress the container in order to force a volume of the initial sweat in the container out of an ejection port of the container, and measure a start time of actuation of the pump and a refill time of the container with an additional sweat to determine the sweat rate.

According to some examples, example systems to monitor a sweat rate of an area of a skin are described. An example system may include a sweat rate monitor and a processor. The sweat rate monitor may include a container, one or more continuity sensors attached to the container, a support ring that encapsulates the container, and an actuator to compress or expand the container. The container may be configured to capture an initial sweat that comes out of a surface of the skin. The processor may be communicatively coupled to the sweat rate monitor. The processor may be further configured to detect the container as filled with the initial sweat, activate the actuator to compress the container to force a volume of the initial sweat in the container out of an ejection port of the container and to expand the container in order to allow room for additional sweat in response to a detection of the volume of the initial sweat as forced out of the ejection port, and determine the sweat rate based on a refill time detected in response to refilling of the container with the additional sweat.

The foregoing summary is illustrative only and is not intended to be in any way limiting. In addition to the illustrative aspects, examples, and features described above, further aspects, examples, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

DETAILED DESCRIPTION

Figure 1A:
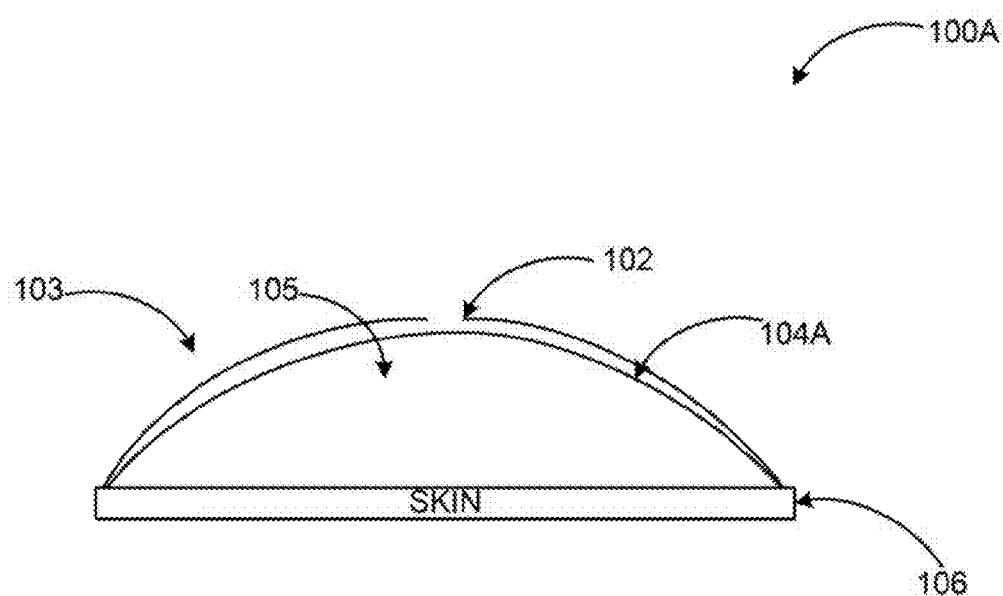
FIG. 1A and FIG. 1B illustrate conceptual diagrams of a sweat rate monitor configured to monitor a sweat rate of an area of a skin.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be used, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn to, inter alia, methods, apparatus, systems, and/or devices to monitor a sweat rate of an area of a skin.

Briefly stated, technologies are generally described to monitor a sweat rate of an area of a skin. A hydration status of a human or non-human entity is monitored based on the sweat rate. The sweat rate is monitored when the sweat rate monitor is detected as sealed against the surface of the skin. The sweat rate monitor is attached to the surface of the skin with an adhesive, or a tape among other schemes to hold the sweat rate monitor in place during a measurement. The sweat rate monitor includes a container to capture an initial amount of sweat that comes out of the surface of the skin. When, the container is detected as filled with the initial amount of sweat, a pump of the sweat rate monitor is actuated to compress the container. The container is compressed to force a volume of the initial amount of sweat in the container out of an ejection port of the sweat rate monitor.

Figure 1B:
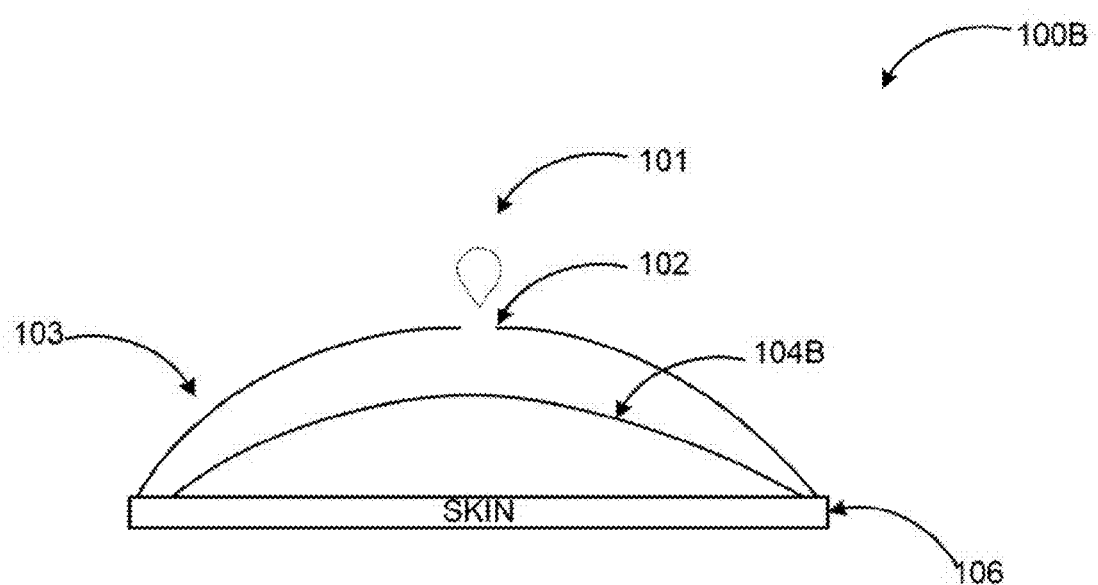

FIG. 1A and FIG. 1B illustrate conceptual diagrams of a sweat rate monitor configured to monitor a sweat rate of an area of a skin, according to at least some examples disclosed herein.

As illustrated by a conceptual diagram 100A, a sweat rate of a skin 106 may be measured when a sweat rate monitor 103 may be detected as sealed against the surface of a skin 106. In some examples, the sweat rate monitor 103 may be a sweat rate monitoring sensor. The sweat rate monitor 103 may be made of flexible components to conform to contour changes on the surface of the skin 106.

The sweat rate monitor 103 may operate by moving volumes of sweat at regular intervals through use of electromechanical actuation. In an example scenario, the sweat rate monitor 103 may force a volume 101 of an initial sweat 105 in response to an actuation of a pump to empty the container 104A that is filled with the initial sweat 105. Other examples of electromechanical actuation devices may include a solenoid electromagnet, an amplified piezo actuator, a servo motor, a bimorph strip, or a shape memory alloy actuator, among others.

In an example scenario, the sweat rate monitor 103 may measure a 1 $cm^2$ of a surface of the skin 106. The measured surface area of the skin 106 may not be limited to 1 $cm^2$. The measured surface area may be depended on a size of the sweat rate monitor 103.

The sweat rate monitor 103 may include a container 104A that may seal the measured area of the surface of the skin 106. The sweat rate monitor 103 may capture the initial sweat 105 that comes out of the skin 106. In response to a detection of the container 104A as filled with the initial sweat 105, a pump of the sweat rate monitor 103 may be actuated to compress the container 104A. A start time of an actuation of the pump may be recorded.

In an example scenario, an amount of the initial sweat 101 may include 100 μL. The amount of the initial sweat 101 may be limited based on a capacity of the container 104A. The pump may force out 5 μL as the volume 101 of the initial sweat 105 expelled from the container 104B. Examples of the volume 101 of the initial sweat 105 and the amount of the initial sweat 105 were not provided in a limiting sense. The volume 101 expelled from the container 104B and the initial sweat 105 used to fill the container 104A may include other amounts. In addition, the sweat monitoring sensor may have a cylindrical shape, among others.

As illustrated by a conceptual diagram 100B, in response to a determination that a container 104B is filled with the initial sweat 105, the pump of the sweat rate monitor 103 may compress the container 104B to force the volume 101 out of an ejection port 102 of the sweat rate monitor 103. A measurement may be taken of a refill time of the container 104B with an additional sweat. The start time of the actuation of the pump, the refill time of the container, and an amount of the volume 101 may be used to compute a sweat rate of the surface of the skin 106. In an example scenario, a volume 101 of the initial sweat 105 may be adjustable between 4 μL and 7 μL, among other volume ranges less than an amount of the initial sweat 105.

In some examples, the container 104A and the container 104B may be constructed from a silicone membrane, or another chemical composition. The silicone membrane may be treated with a hydrophobic material, for example. The silicone membrane may contact the surface of the skin 106. The hydrophobic material may force the initial sweat 105 and additional sweat to migrate from the surface of the skin 106 into the silicone membrane.

Figure 2:
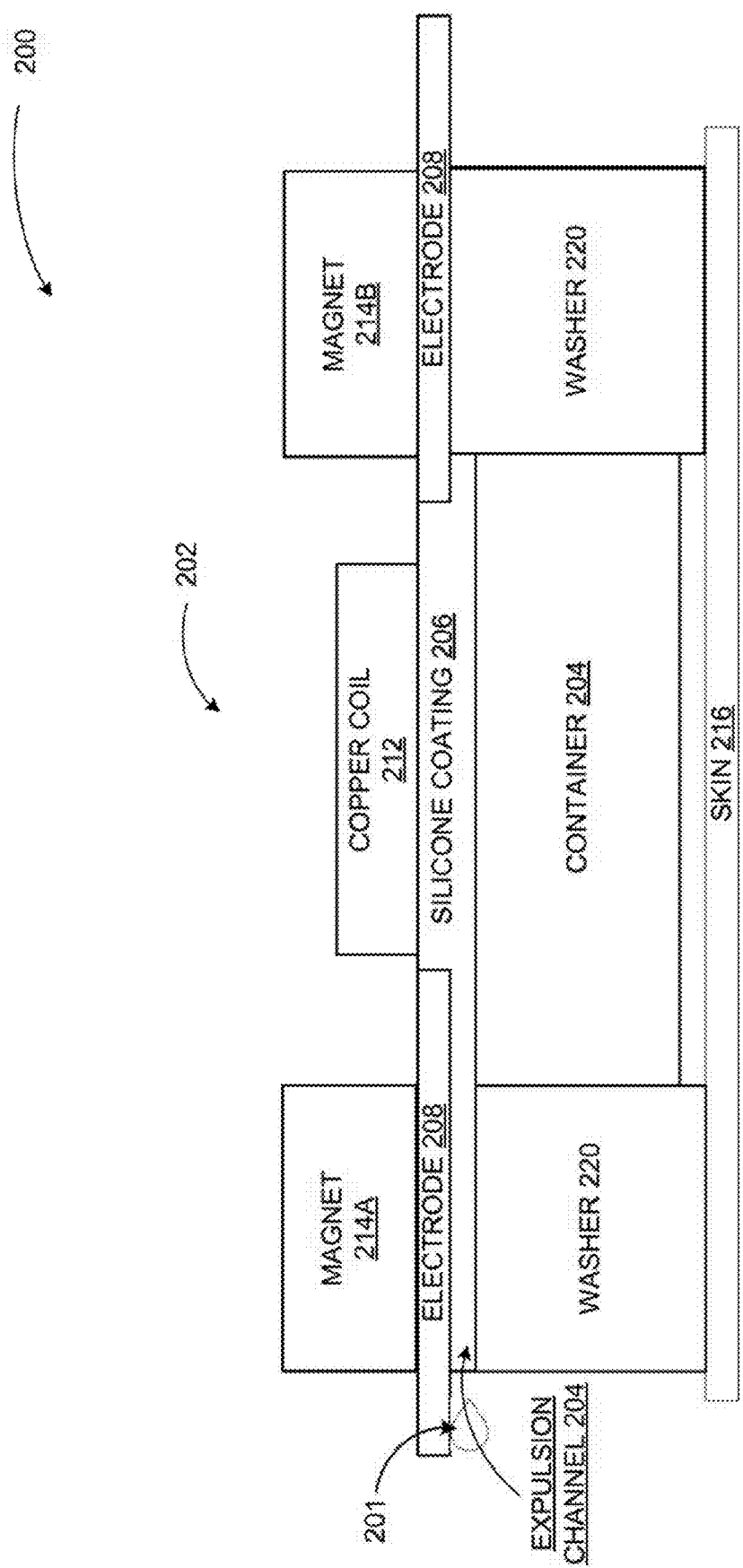
FIG. 2 illustrates components of a sweat rate monitor configured to monitor a sweat rate of an area of a skin.

FIG. 2 illustrates components of a sweat rate monitor configured to monitor a sweat rate of an area of a skin, according to at least some examples disclosed herein.

In a diagram 200, a sweat rate monitor 202 may include components such as a magnet 214A, a coil 212, and a magnet 214B. The coil 212 may be a copper coil or a coil made out of another material that may move as a result of a changing magnetic field. The magnet 214A, the coil 212, and the magnet 214B may be configured to contact a silicone coating 206. The silicone coating 206 may form a container 204 by encapsulating an adjustable volume within a washer 220. The coil 212 may be attached to the silicone coating 206 via a gel adhesive or another adhesive material.

In some examples, the magnet 214A and the magnet 214B may comprise neodymium. The magnet 214A and the magnet 214B may be attached to a top section of a container 204. The magnet 214A and the magnet 214B may actuate the coil 212 to compress and/or to expand the container 204.

Electrodes 208 may be inserted into the silicone coating 206 of the container 204 to detect the container 204 as filled with sweat or to actuate the coil 212. The electrodes 208 may be constructed from aluminum, copper, among other materials. In some examples, the electrodes 208 may detect the container 204 as filled with an initial sweat. The electrodes 208 may activate the magnets 214A and 214B to have the magnets 214A and 214B actuate the coil 212. The actuated coil 212 may compress the container 204 and force a volume 201 from the container 204. The volume 201 may be ejected from an expulsion channel 204. The expulsion channel 204 may end in a hydrophobic ejection port.

The silicone coating 204 may contact a surface of a skin 216. The silicone coating 206 of the container 204 may be treated with a hydrophobic layer. The hydrophobic layer may force the initial sweat and an additional sweat to migrate from the surface of the skin 216 into the container 204.

Figure 3:
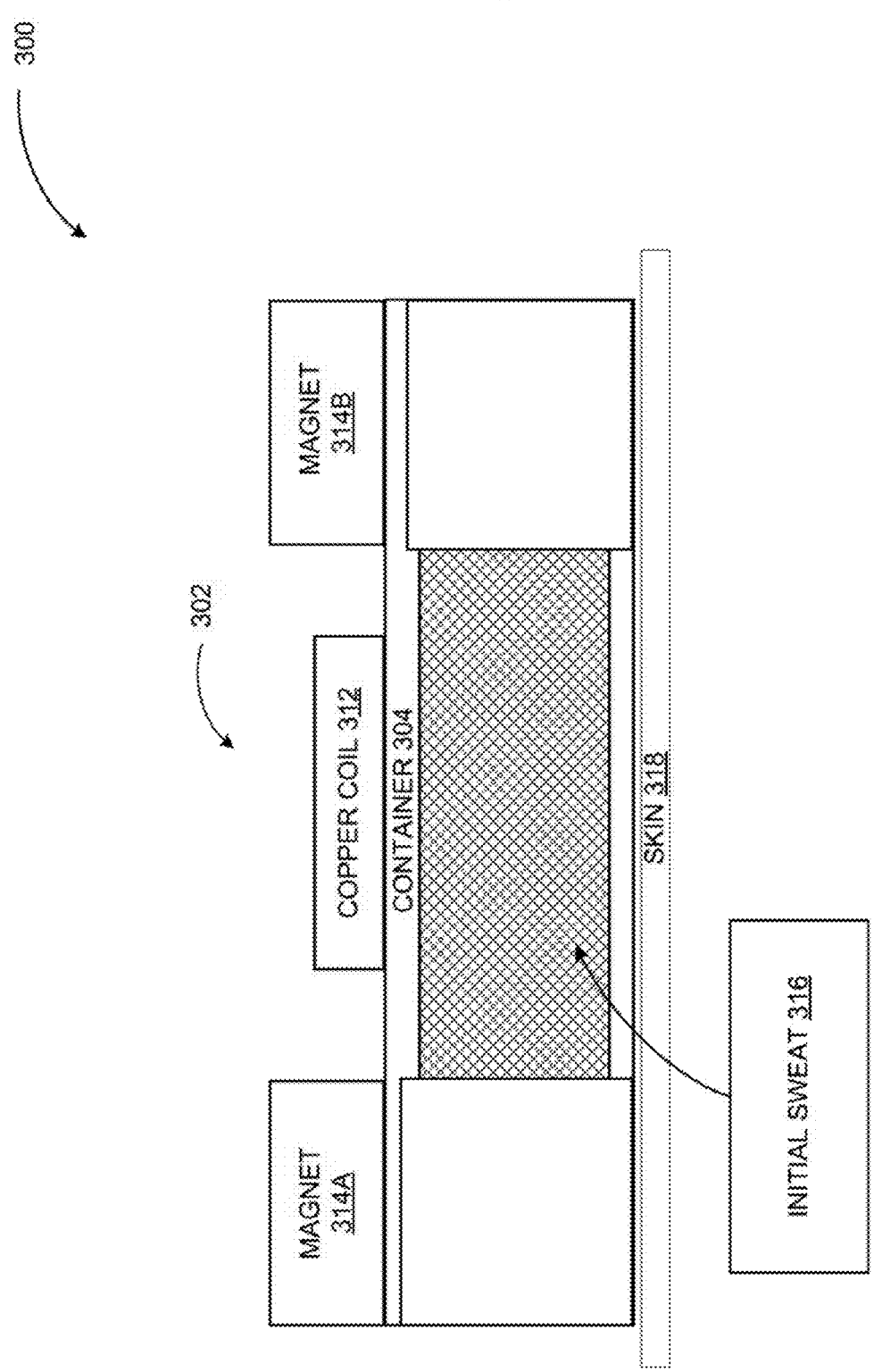
FIG. 3 illustrates a diagram of a container of a sweat rate monitor filled with an initial amount of sweat.

FIG. 3 illustrates a diagram of a container of a sweat rate monitor filled with an initial amount of sweat, according to at least some examples disclosed herein.

In the diagram 300, a sweat rate monitor 302 may include a magnet 314A, a coil 312, a magnet 314B, and a container 304. The magnet 314A, the coil 312, the magnet 314B may be attached to the container 304. The container 304 may be attached to a surface of a skin 318.

The container 304 may be filled with an initial sweat 316 that pours out of the skin 318. In some examples, a continuity sensor inserted into the container 304 may be used to detect a fill state of the container 304. In response to a detection that the container 304 is filled with the initial sweat 304, the magnet 314A and the magnet 314B may be activated to actuate the coil 312. The coil 312 may be configured to expand and compress the container 304 to force a volume from the initial sweat 318 out of the container 304.

Figure 4:
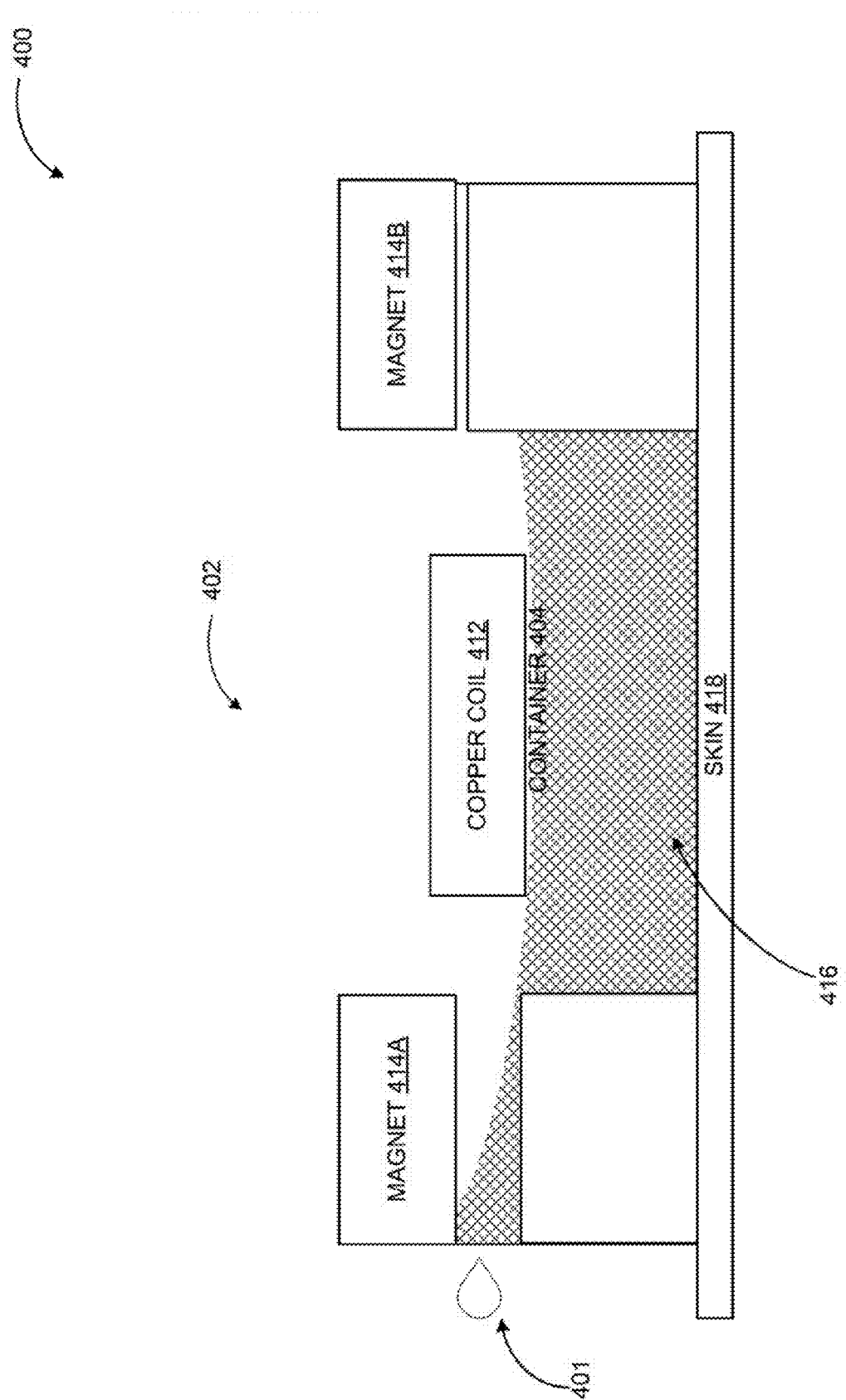
FIG. 4 illustrates a diagram of removal of a partial volume of an initial amount of sweat from a container of a sweat rate monitor.

FIG. 4 illustrates a diagram of removal of a partial volume of an initial amount of sweat from a container of a sweat rate monitor, according to at least some examples disclosed herein.

In the diagram 400, a sweat rate monitor 402 may include components such as a magnet 414A, a coil 412, a magnet 414B, and a container 404. The sweat rate monitor 402 may seal against a surface of a skin 418. In an example scenario, the sweat rate monitor 402 may be attached against a surface of a skin with an adhesive or some other material that may prevent detachment of the sweat rate monitor 402 from the skin without an application of force. The sweat rate monitor 402 may also detect the container 404 as filled with an initial sweat 416 through a continuity sensor. In response, the magnet 414A and the magnet 414B may be activated. The activated magnets may actuate the coil 412. The coil 412 may expand and compress the container 414. A volume 401 of the initial sweat 416 may be forced out of the container 404 through an expulsion channel in the sweat rate monitor 402. The expulsion channel may be hydrophobic. The expulsion channel may be carved into a support ring encapsulating the container 404. The support ring may be coated in a silicone-based material. The volume 401 of the initial sweat 416 may be forced out of the container 404 from an ejection port on the sweat rate monitor 416.

The components of the sweat rate monitor 402 that includes the magnet 414A, the magnet 414B, the coil, the expulsion channel, and the ejection port may be referred to as a pump of the sweat rate monitor 402. A start time may be recorded in response to actuating the pump to force out the volume 401 of the initial sweat 416. The coil 412 may be contracted by deactivating the magnet 414A and the magnet 414B after an ejection duration that correlates to a time to force out the volume 401 of the initial sweat 416. The container 404 may refill with additional sweat in response to the contraction of the coil 412. The continuity sensor may detect the container 404 as refilled with the additional sweat. In response, a refill time may be recorded that captures time to refill the container 404 with the additional sweat that pours from the skin 418. The start time, the refill time, and an amount of the volume 401 may be used to compute the sweat rate.

Figure 5:
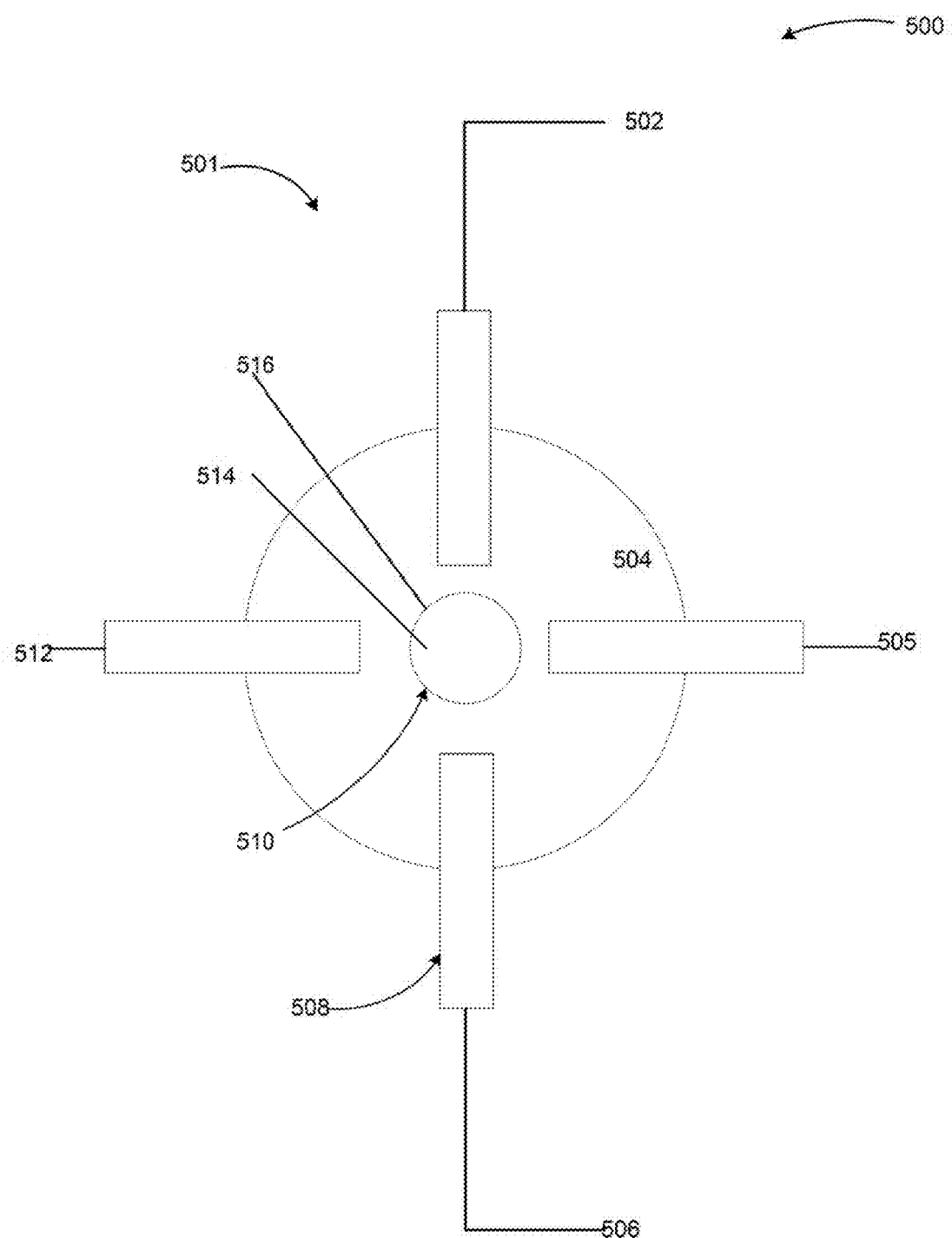
FIG. 5 illustrates a wire diagram of sensors of a sweat rate monitor.

FIG. 5 illustrates a wire diagram of sensors of a sweat rate monitor, arranged in accordance with at least some examples disclosed herein.

In an example scenario, a wire diagram 500 of a sweat rate monitor 501 may illustrate sensors that may include analog inputs 502, 505, 506, a digital output 516, a $V_{CC}$ pin 512, a ground sensor 514, a coil 510, and an electrode 508. The analog inputs 502, 505, 506 may be inserted within a depth into the container 504. The depth may be 0.1 mm or another length. Additionally, a coil 510 may be a coil, but may include additional chemical compositions.

The coil 510 may be configured to force down out of a bore of a ring magnet to force a volume of an initial sweat out of the container 504 in response to a detection of the container 504 as filled with the initial sweat. The electrode 508 may be configured to facilitate compression of the container 504. The coil 510 may be retracted to expand the container 504. In response, the container 504 may be expanded to refill the container 504 with an additional sweat to refill the volume of the initial sweat that was ejected out of the ejection port. A start time of ejection of the volume of the initial sweat and a refill time to refill the container 504 with additional sweat may be recorded. In some examples, the sensors may be integrated into a computing device by the analog inputs 502, 504, 506, the digital output 516, and the $V_{CC}$ pin 512. The computing device may cause the coil 510 to force down and compress by transmitting instructions to the sweat rate monitor 501.

Figure 6A:
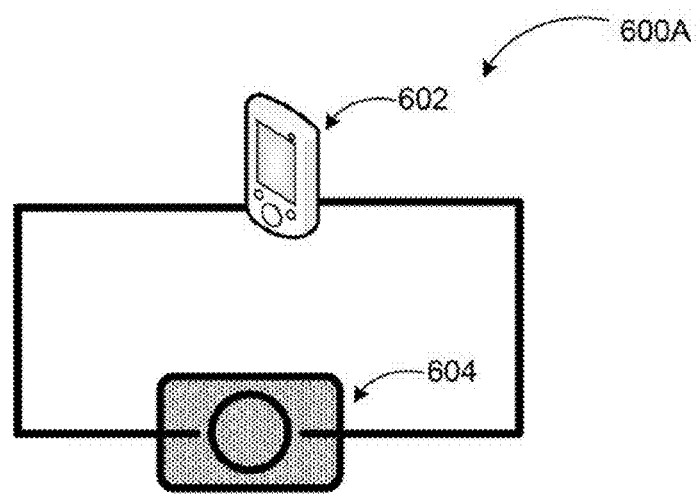
FIG. 6A, FIG. 6B, and FIG. 6C illustrate communications with a sweat rate monitor.
Figure 6B:
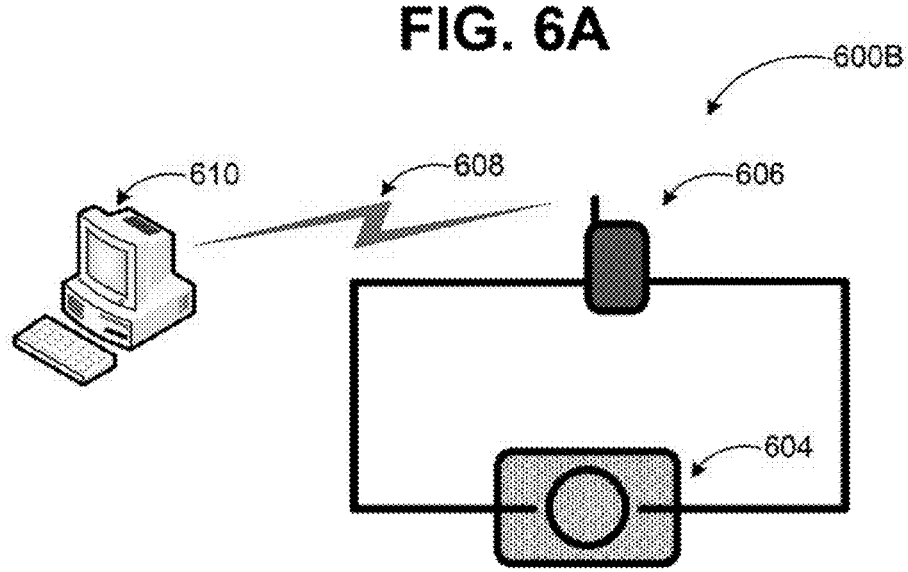
Figure 6C:
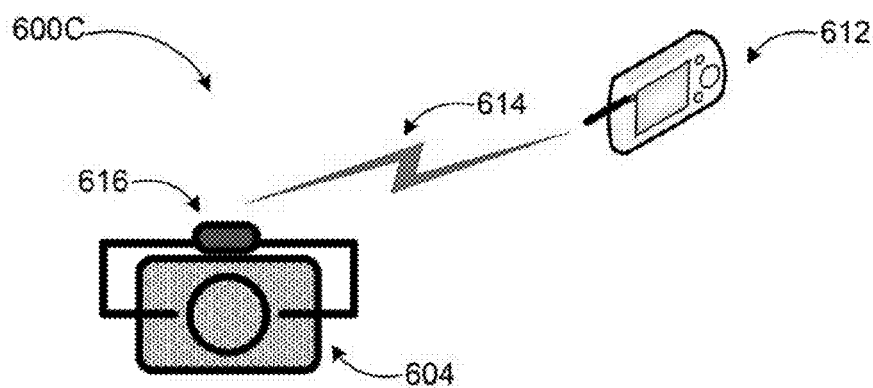

FIG. 6A, FIG. 6B, and FIG. 6C illustrate communications with a sweat rate monitor, according to at least some examples disclosed herein.

A diagram 600A, a diagram 600B, and a diagram 600C illustrate example communication systems with a sweat rate monitor. Sweat rate may be monitored through the sweat rate monitor. The sweat rate monitor may be implemented through a variety of systems, as illustrated in the diagram 600A, the diagram 600B, and the diagram 600C.

The diagram 600A illustrates a sweat rate monitor 604, which may include a sweat rate monitor module. The sweat rate monitor 604 may be implemented as a self-contained device that may be configured to store and/or transmit sweat rate data to remote computing devices, such as a multi-component device 602. The multi-component device 602 may electrically or wirelessly couple to remote computing devices. In some examples, the multi-component device 602 may be coupled directly to a general purpose/specialized computing device, which may be configured to perform tasks of the sweat rate monitor module.

In the diagram 600B, the sweat rate monitor 604 and sweat rate monitor module 606 may be housed separately. The sweat rate monitor 604 may be electrically coupled to the sweat rate monitor module 606. The sweat rate monitor module 606 may be configured to communicate with a computing device 610 through a wireless communication 608 or through an electrical connection. The sweat rate monitor module 606 may be configured to provide measurement results from the sweat rate monitor 604 to the computing device 610.

The sweat rate monitor module 606 may also be configured to receive control parameters from the sweat rate monitor 604 and provide the control parameters to the computing device 610. According to an example implementation, the sweat rate monitor 604 may be coupled to the sweat rate monitor module 606 through a flexible strap. The flexible strap may be placed on an arm, a leg, or a torso with the sweat rate monitor module 606 located on an opposite side of the flexible strap.

The diagram 600C may include the sweat rate monitor 604 and sweat rate monitor module 616. The sweat rate monitor 604 may include transmission lines and a dielectric substrate. The sweat rate monitor 604 may be electrically coupled to the sweat rate monitor module 616. The sweat rate monitor 604 coupled to the sweat rate monitor module 616 may be considered a device.

In an example scenario, the device may be configured to communicate with a remote computing device 612 through a wireless communication 614 or through an electrical connection. The device may be placed on the area of the skin near capillary beds. A location of the capillary bed in a human body marks a point where circulation reaches a terminus and loops back around to allow blood to pass through the heart and become re-oxygenated so the blood may return to circulation. Additionally, at a location of the capillary beds, fresh blood drops off water, oxygen, and nutrients. Also at the location of the capillary beds, waste materials (i.e. carbon dioxide) may be collected from cells so that the waste materials may be expunged from the body. Common locations of the capillary beds may include fingertips, earlobes, and a forehead, among other locations.

In some examples, the device may be placed on the area of the skin and may collect data from the area of the skin. The data may include location data, which may be collected through use of a Global Positioning Service (GPS) and may also include sensor-driven data. The sensor-driven data may include, among other things, presence data, hydration data, sweat rate data, heart rate data, and blood pressure data. The location data and the sensor-driven data may be transmitted from the device to the remote computing device 612.

In additional examples, the device may be wearable through a flexible strap, as explained in the diagram 600B. The device may be wearable through other methods, such as through adhesives, as well. The sweat rate monitor may be wearable, as well. The device and/or the sweat rate monitor may be configured as a monitoring device, a health monitoring device and/or an athletic monitoring device, and a physiological sensor, among others. The health monitoring device and/or the athletic monitoring device may include a watch, a heart-rate monitoring device, an electroencephalography device, a wireless real-time location and/or tracking device, an adhesive applied to the area of the skin, a stretchable adhesive sweat rate monitor applied to the area of the skin, and a physiological sensor, among other things. In some examples, the physiological sensor may be located on one of a belt, an ankle device, a wrist device, and an electroencephalography device, among others.

The device may also be configured to communicate wirelessly with the remote computing device 612 to provide the collected data. The stored information may be downloaded by another device. The example communication systems of the diagram 600A, the diagram 600B, and the diagram 600C may perform additional tasks, which may include formatting, analysis, and reporting of the collected data. In an example scenario, an alarm mechanism may be set, such that in response to a determination that the sweat rate is in excess of a predefined threshold, the system may alert a person using the system, a healthcare provider, or another designated person. Furthermore, determined sweat rate may be displayed on the system, at a remote location, or on an output to a designated target, such as a printer.

Each of the computing devices described in the diagram 600A, the diagram 600B, and the diagram 600C, such as the computing device 610 and the remote computing device 612, may be a general purpose computing device or a special purpose computing device. The examples in the diagram 600A, the diagram 600B, and the diagram 600C were not provided in limiting sense. The sweat rate monitor may be deployed in other arrangements or configurations.

Figure 7A:
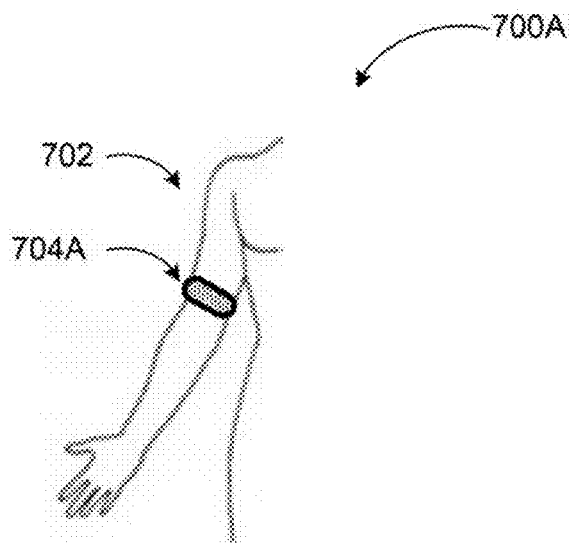
FIG. 7A and FIG. 7B illustrate placement of a sweat rate monitor in different locations of a body on a skin.
Figure 7B:
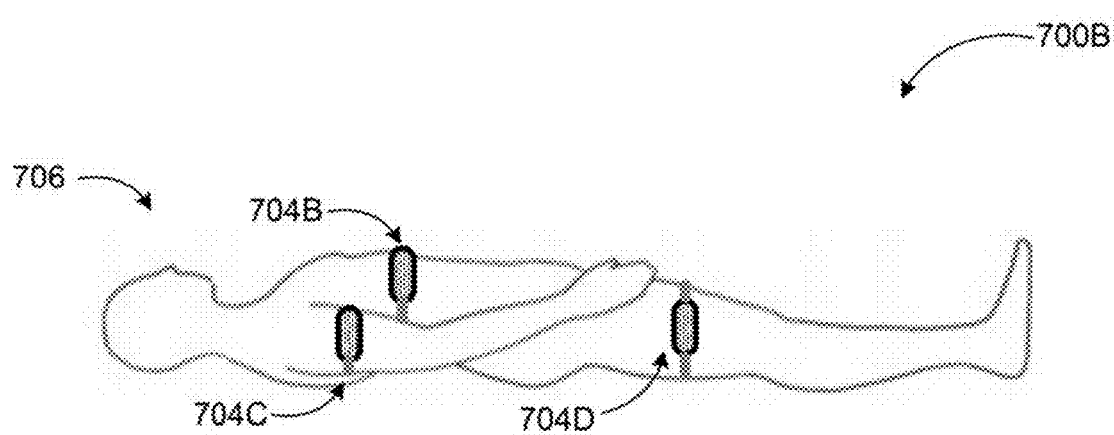

FIG. 7A and FIG. 7B illustrate placement of a sweat rate monitor in different locations of a body on a skin, according to at least some examples disclosed herein.

A diagram 700A in FIG. 7A illustrates the sweat rate monitor 704A of a hydration monitoring system. The sweat rate monitor 704A may be placed on the area of the skin of an arm 702 of a human body. In an example scenario, the sweat rate monitor 704A may be placed on an inside of the area of the skin of an arm 702 below an arm pit. The region of placement for the sweat rate monitor 704A has a smaller change in the dilation/constriction of peripheral blood vessels, which the body uses for temperature regulation. Flow of blood through the peripheral blood vessels is an indication of level of body hydration, among other things. The sweat rate monitor 704A may also be mounted on other areas of a skin of a human being.

A diagram 700B in FIG. 7B illustrates additional example locations on an area of a skin on an arm 704C, on a leg 704D, and on a torso 704B of a human body 706 for placement of the sweat rate monitor. The sweat rate monitor may also be placed in other suitable locations on the human body. The sweat rate monitor may also be used to determine sweat rate of non-human beings.

Figure 8:
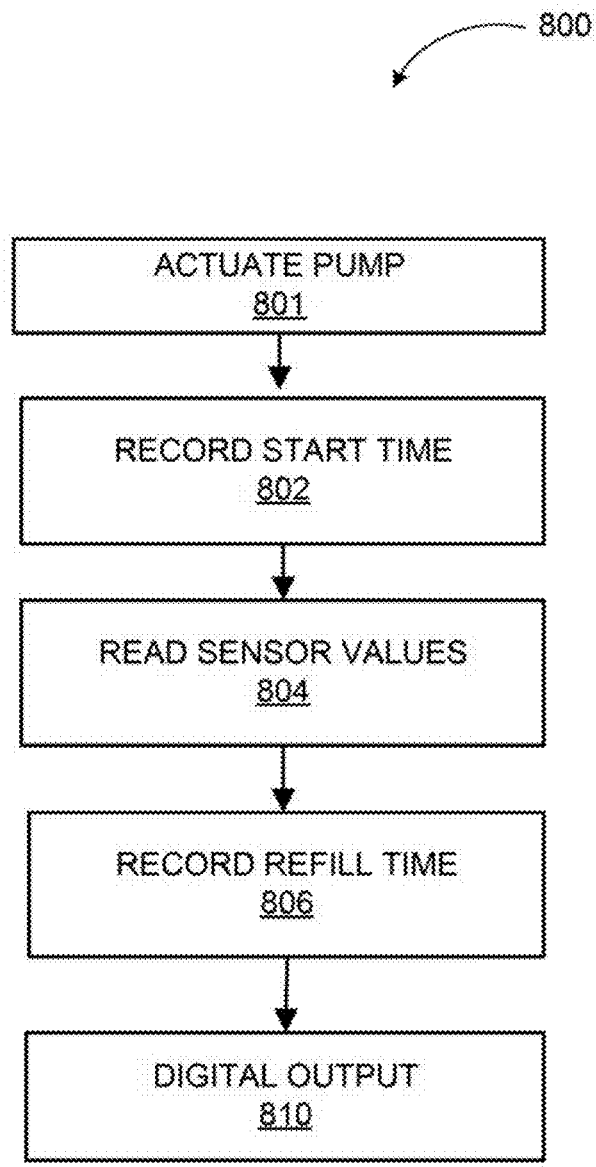
FIG. 8 illustrates a flow diagram of processes to monitor a sweat rate of an area of a skin with a sweat rate monitor.

FIG. 8 illustrates a flow diagram of processes to monitor a sweat rate of an area of a skin with a sweat rate monitor, according to at least some examples disclosed herein.

The flow diagram 800 may start with a process to actuate a pump 801. The pump may include components such as magnets, a coil, and an expulsion channel of a sweat rate monitor. The pump may be used to force out a volume of an initial sweat that fills a container of the sweat rate monitor. The container may be detected as filled with the initial sweat through a continuity sensor of the sweat rate monitor. A start time may be recorded 802 in response to actuation of the pump.

Sensor values 804 may be continuously read to detect the container as refilled with an additional sweat to refill the volume of the initial sweat that was expelled. In response to a detection that the container is refilled, a refill time may be recorded 806. The start time, the refill time, an amount of the volume of the initial sweat may be used to compute a sweat rate. The sweat rate may be output digitally 810. The digital output 810 may be provided to a display module. The display module may be a user interface, for example, and may be located on a computing device.

The container may be compressed in response to a detection of a sweat continuity between the sensors of the sweat rate monitor. A full state of the container may be inferred based on the detection of the sweat continuity. Identification of a full container may help assure that a consistent volume of sweat is ejected from the ejection port, and may improve accuracy of sweat volume measurements. A partially filled container may introduce variability to the volume of the ejected sweat. A full container may assure a same volume of sweat ejected from the container with each compression of the container.

The fixed channel diameter of the ejection port and a force applied to the container may control a displacement of the volume of ejected sweat. The volume of the ejected sweat may be a fraction of a capacity of the container. Timestamps may be recorded with each instance of the compression of the container to expel the volume of the sweat.

An average flow of the sweat may be computed using the timestamps associated with the ejection of the volume of sweat. The volume of the sweat may be inversely related with an accuracy of the flow rate of the sweat. A smaller volume of the ejected sweat over a shorter time period may be used to measure a more accurate flow rate of the sweat. A sweat rate monitor with a sufficient low ejection volume may measure sweat rate at a real time.

In an example scenario, the pump of the sweat rate monitor may actuate in a circular time period (i.e.: 1-10 seconds) for exercising humans who sweat at standard sweat rates. The sweat rate monitor may have an expulsion volume within an order of a microliter. The container may have an area within an order of a square centimeter. The sweat rate may be computed as an average value of the volume of the ejected sweat over the time periods of a number of previous compressions (i.e.: 10 to 20 compressions). The sweat rate may be computed over a time period such as 1 to 2 minutes.

A hydrophobic ejection port may be used to prevent a leakage of the sweat from the container. The sweat may be expelled as a result of a compression on the container. The pump may be actuated to compress the container as a result of the coil that is forced down out of a bore of the ring magnet on the top of the sweat rate monitor. The container may be uncompressed as a result of a deactivated pump. The deactivate pump may allow the coil to retract back to the bore of the ring magnet.

Figure 9:
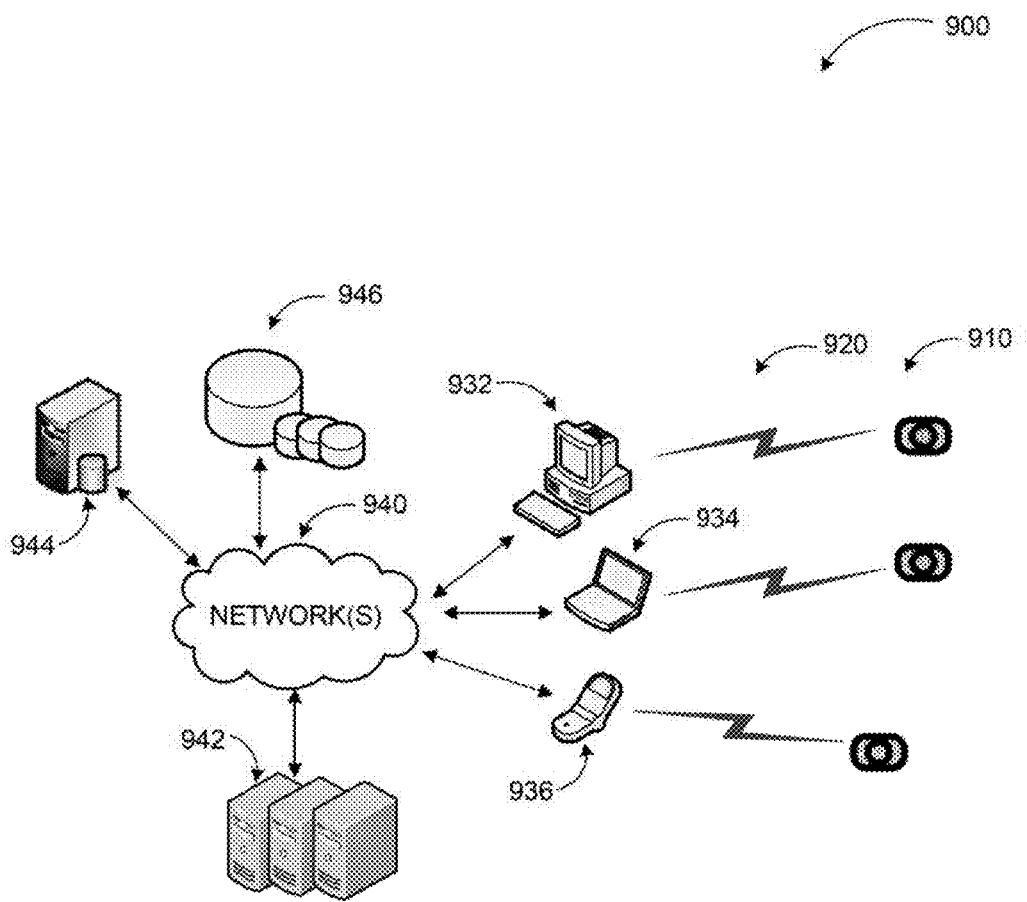
FIG. 9 illustrates a networked environment, where a system to monitor a sweat rate of an area of a skin with a sweat rate monitor.

FIG. 9 illustrates a networked environment, where a system to monitor a sweat rate of an area of a skin with a sweat rate monitor, according to at least some examples disclosed herein.

The networked environment of a diagram 900 illustrates the system to monitor the sweat rate of the area of the skin through use of the sweat rate monitor. The system may be implemented through separate applications, one or more integrated applications, one or more centralized services, or one or more distributed services on one more computing devices. The diagram 900 illustrates an example of a distributed system implementation through networks 940.

As discussed previously, a sweat rate monitor module 910 of the sweat rate monitor may be configured to monitor sweat rate. The sweat rate monitor module 910 may be electrically coupled to computing devices 932, 934, and 936. In some examples, the sweat rate monitor module 910 may be part of a self-sufficient package that includes the sweat rate monitor module, and may be configured to provide feedback to the respective computing devices through direct connection of wireless connection 920.

The computing devices 932, 934, and 936 may be configured to determine sweat rate and provide information associated with the sweat rate to a monitoring service executed on one or more of servers 942. According to other examples, the monitoring service may be executed on the one or more of the servers 942 and may be configured to directly control the operations of the sweat rate monitor module 910 through network(s) 940. For example, data associated with the sweat rate measurements and other data associated with the operation of the monitoring system may be stored in one or more data stores, such as data stores 946, and may be directly accessible through the network(s) 940. In other examples, the data stores 946 may be managed by a database server 944.

In some examples, the network(s) 940 may comprise any topology of servers, clients, switches, routers, modems, Internet service providers (ISPs), and any appropriate communication media (e.g., wired or wireless communications). A system according to examples may have a static or dynamic network topology. The network(s) 940 may include a secure network such as an enterprise network (e.g., a LAN, WAN, or WLAN), an unsecure network such as a wireless open network (e.g., IEEE 802.11 wireless networks), or a world-wide network such (e.g., the Internet). The network(s) 940 may also comprise a distinct networks that are adapted to operate together. The network(s) 940 are configured to provide communication between the nodes. By way of example, and not limitation, the network(s) 940 may include wireless media such as acoustic, RF, infrared and other wireless media. Furthermore, the network(s) 940 may be portions of the same network or separate networks.

Example examples may also include methods. These methods can be implemented in any number of ways, including the structures described herein. One such way is by machine operations, of devices of the type described in the present disclosure. Another optional way is for one or more of the individual operations of the methods to be performed in conjunction with one or more human operators performing some of the operations while other operations are performed by machines. These human operators need not be collocated with each other, but each can be only with a machine that performs a portion of the program. In other examples, the human interaction can be automated such as by pre-selected criteria that are machine automated.

A wearable sweat rate monitor may help monitor the sweat rate of an area of a skin and, in turn, help monitor a hydration status of a human. This type of wearable sensor may have applications outside of athletic and human health monitoring, as it may be applied to situations where a small fluid flow from a defined area is to be measured. The wearable sweat rate monitor may have broad environmental, microfluidic, analytical and/or other applications.

The examples in FIG. 1 through FIG. 9 have been described using specific apparatuses, configurations, and systems for monitoring the sweat rate of the area of the skin by use of a wearable sweat rate monitor. Examples for monitoring the sweat rate of the area of the skin are not limited to the specific apparatuses, configurations, and systems according to these examples.

Figure 10:
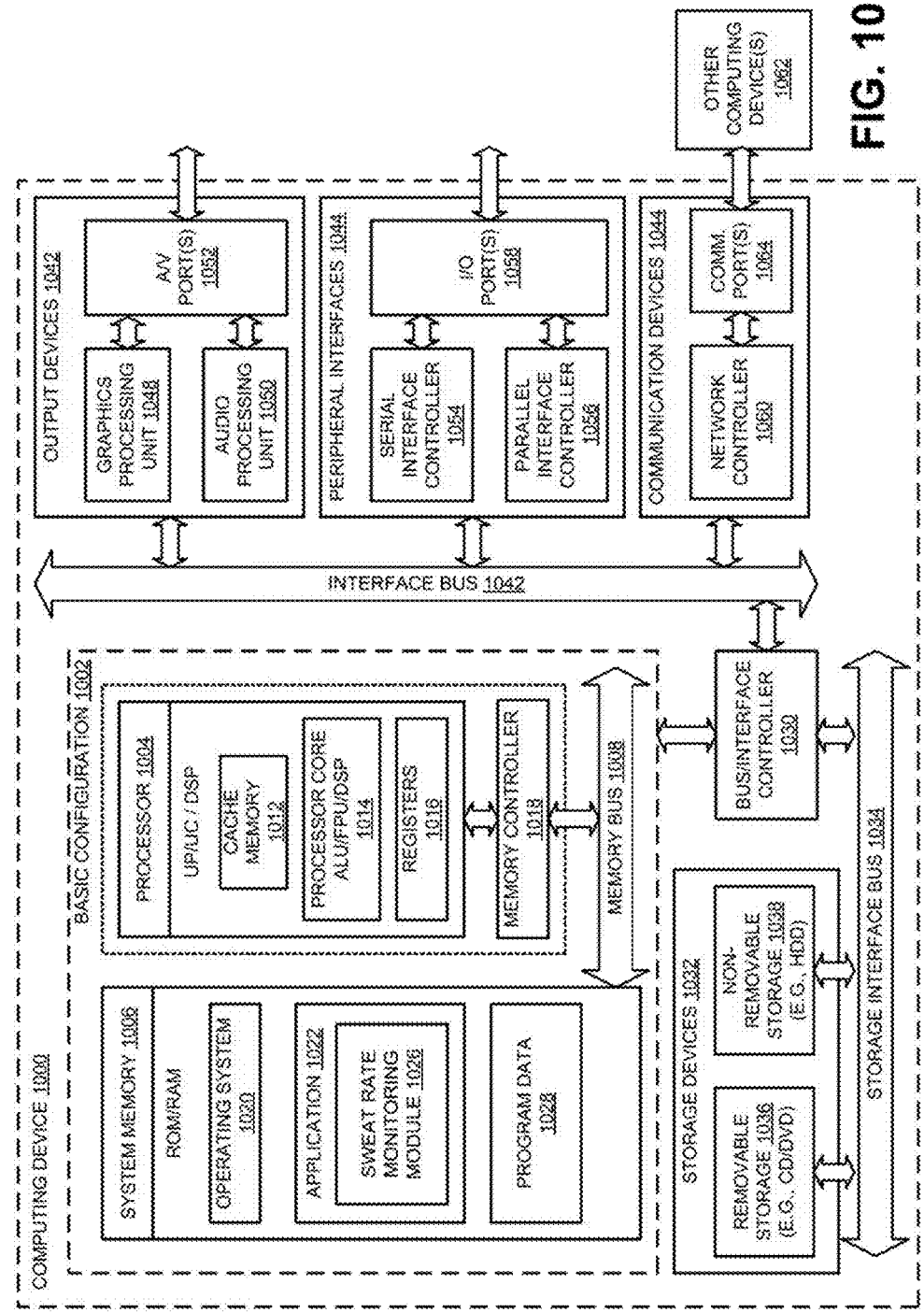
FIG. 10 illustrates a general purpose computing device, which may be used to monitor a sweat rate of an area of a skin with a sweat rate monitor.

FIG. 10 illustrates a illustrates a general purpose computing device, which may be used to monitor a sweat rate of an area of a skin with a sweat rate monitor, arranged in accordance with at least some examples described herein.

The computing device 1000 may be used as a server, desktop computer, portable computer, smart phone, special purpose computer, or similar device such as a controller, a new component, a cluster of existing components in an operational system including a vehicle and a smart dwelling. In an example basic configuration 1002, the computing device 1000 may include one or more processors 1004 and a system memory 1006. A memory bus 1008 may be used for communicating between the processor 1004 and the system memory 1006. The example basic configuration 1002 is illustrated in FIG. 10 by those components within the inner dashed line.

Depending on the desired configuration, the processor 1004 may be of any type, including but not limited to a microprocessor ($\mu$P), a microcontroller ($\mu$C), a digital signal processor (DSP), or any combination thereof. The processor 1004 may include one more levels of caching, such as a level cache memory 1012, one or more processor cores 1014, and registers 1017. The example one or more processor cores 1014 may (each) include an arithmetic logic unit (ALU), a floating point unit (FPU), a digital signal processing core (DSP Core), or any combination thereof. An example memory controller 1018 may also be used with the processor 1004, or in some implementations the example memory controller 1018 may be an internal part of the processor 1004.

Depending on the desired configuration, the system memory 1006 may be of any type including but not limited to volatile memory (such as RAM), non-volatile memory (such as ROM, flash memory, etc.) or any combination thereof. The system memory 1006 may include an operating system 1020, an application 1022, and program data 1024. The application 1022 may include a sweat rate monitor module 1026, which may be an integral part of the application 1022 or may be a separate application on its own. The sweat rate monitor module 1026 may be configured to communicate with a computing device 1000 through a wireless communication or through an electrical connection.

The sweat rate monitor module 1026 may be configured to provide measurement results from a sweat rate monitor to the computing device 1000. The sweat rate monitor module 1026 may also be configured to receive control parameters from the sweat rate monitor and may provide the control parameters to the computing device 1000. The sweat rate monitor may be electrically coupled to the sweat rate monitor module 1026. The sweat rate monitor coupled to the sweat rate monitor module 1026 may be considered a device. The device may be configured to determine sweat rate of an area of a skin. The device may also be configured to communicate wirelessly with a remote computing device to provide determined sweat rate. In some examples, the device may be configured to store the determined sweat rate as the program data 1024. The program data 1024 may be downloaded by another device.

The computing device 1000 may have additional features or functionality, and additional interfaces to facilitate communications between the example basic configuration 1002 and any desired devices and interfaces. For example, a bus/interface controller 1030 may be used to facilitate communications between the example basic configuration 1002 and one or more data storage devices 1032 via a storage interface bus 1034. The data storage devices 1032 may be one or more removable storage devices 1036, one or more non-removable storage devices 1038, or a combination thereof. Examples of the removable storage and the non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

The system memory 1006, the removable storage devices 1036 and the non-removable storage devices 1038 are examples of computer storage media. Computer storage media includes, but is not limited to, RAM, ROM, EEPROM, flash memory or other memory technology, CD-ROM, digital versatile disks (DVDs), solid state drives, or other optical storage, magnetic cassettes, magnetic tape, magnetic disk storage or other magnetic storage devices, or any other medium which may be used to store the desired information and which may be accessed by the computing device 1000. Any such computer storage media may be part of the computing device 1000.

The computing device 1000 may also include an interface bus 1040 for facilitating communication from various interface devices (for example, one or more output devices 1042, one or more peripheral interfaces 1044, and one or more communication devices 1046) to the example basic configuration 1002 via the bus/interface controller 1030. Some of the one or more output devices 1042 include a graphics processing unit 1048 and an audio processing unit 1070, which may be configured to communicate to various external devices such as a display or speakers via one or more A/V ports 1072. One or more peripheral interfaces 1044 may include a serial interface controller 1074 or a parallel interface controller 1076, which may be configured to communicate with external devices such as input devices (for example, keyboard, mouse, pen, voice input device, touch input device, etc.) or other peripheral devices (for example, printer, scanner, etc.) via one or more I/O ports 1078. An example communication device includes a network controller 1060, which may be arranged to facilitate communications with one or more other computing devices 1062 over a network communication link via one or more communication ports 1064. The one or more other computing devices 1062 may include servers, client devices, and comparable devices.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 1000 may be implemented as a part of a general purpose or specialized server, mainframe, or similar computer that includes any of the above functions. The computing device 1000 may also be implemented as a personal computer including both laptop computer and non-laptop computer configurations.

Example examples may also include methods to monitor a sweat rate of the area of the skin. These methods can be implemented in any number of ways, including the structures described herein. One such way may be by machine operations, of devices of the type described in the present disclosure. Another optional way may be for one or more of the individual operations of the methods to be performed in conjunction with one or more human operators performing some of the operations while other operations may be performed by machines. These human operators need not be collocated with each other, but each can be only with a machine that performs a portion of the program. In other examples, the human interaction can be automated such as by pre-selected criteria that may be machine automated.

Figure 11:
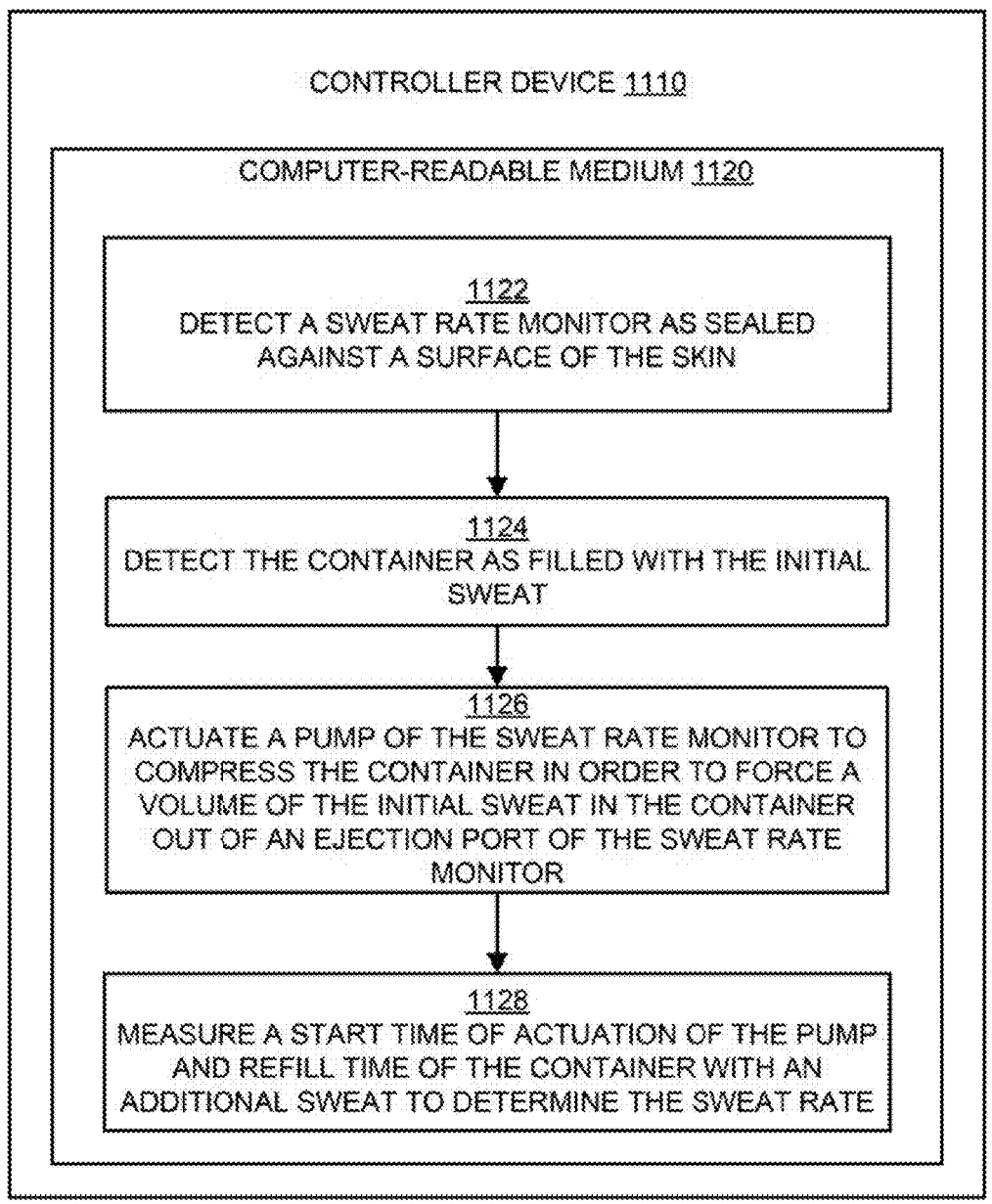
FIG. 11 illustrates a block diagram of an example computer program product, all arranged in accordance with at least some examples described herein.

FIG. 11 is a illustrates a block diagram of an example computer program product, such as the computing device in FIG. 10, arranged in accordance with at least some examples described herein.

Example methods of an example controller device 1110 may include one or more operations, functions or actions as illustrated by one or more of blocks 1122, 1124, 1126, and 1128. The operations described in the blocks 1122 through 1126 may also be stored as computer-executable instructions in a computer-readable medium such as a computer-readable medium of a computing device 1000.

An example process to monitor a sweat rate of an area of a skin may begin with block 1122, "DETECT A SWEAT RATE MONITOR AS SEALED AGAINST A SURFACE OF THE SKIN," where the sweat rate monitor includes a container to capture an initial sweat that comes out of the surface of the skin. In some examples, the container may be a silicone membrane. The silicone membrane may be treated with a hydrophobic material. The silicone membrane may contact the surface of the skin, which may force the initial sweat and additional sweat to migrate from the surface of the skin into the silicone membrane.

Block 1122 may be followed by block 1124, "DETECT THE CONTAINER AS FILLED WITH THE INITIAL SWEAT," where a volume of the initial sweat may be adjustable between about 4 μL and about 7 μL.

Block 1124 may be followed by block 1126, "ACTUATE A PUMP OF THE SWEAT RATE MONITOR TO COMPRESS THE CONTAINER IN ORDER TO FORCE A VOLUME OF THE INITIAL SWEAT IN THE CONTAINER OUT OF AN EJECTION PORT OF THE SWEAT RATE MONITOR," where a start time of an actuation of a pump of the sweat monitoring sensor may be measured. In response to a determination that the container becomes filled with the initial sweat, the pump of the sweat rate monitor may compress the container to force a volume of the initial sweat out of an ejection port of the sweat rate monitor.

Block 1126 may be followed by block 1128, "MEASURE A START TIME OF ACTUATION OF THE PUMP AND A REFILL TIME OF THE CONTAINER WITH AN ADDITIONAL SWEAT TO DETERMINE THE SWEAT RATE," where a measurement of the start time of the actuation of the pump may be taken and a measurement of the refill time of the container may be taken to determine the sweat rate.

The blocks included in the above described process are for monitoring a sweat rate of the area of the skin. In some examples, the blocks may be performed in a different order. In some other examples, various blocks may be eliminated. In still other examples, various blocks may be divided into additional blocks, or combined together into fewer blocks.

According to some examples, a method to monitor a sweat rate of an area of a skin may be described. The method may include detecting a sweat rate monitor as sealed against a surface of the skin, wherein the sweat rate monitor includes a container to capture an initial sweat that comes out of the surface of the skin, detecting the container as filled with the initial sweat, actuating a pump of the sweat rate monitor to compress the container in order to force a volume of the initial sweat in the container out of an ejection port of the sweat rate monitor, and measuring a start time of actuation of the pump and a refill time of the container with an additional sweat to determine the sweat rate.

According to further examples, the method may further include forcing the volume of the initial sweat in the container through a hydrophobic ejection port. The volume of the initial sweat is adjustable between about 4 µL and about 7 µL. A silicone membrane may be utilized as the container. The silicone membrane is treated with a hydrophobic material on a surface of the silicone membrane lining the surface of the skin to force the initial sweat and the additional sweat to migrate from the skin into the silicone membrane. A coil located on a top section and a center section of the sweat rate monitor may be forced down to compress the container in response to a detection of the container as filled with the initial sweat. The volume of the initial sweat may be forced out of the ejection port through an expulsion channel carved into a support ring that encapsulates the container. A continuity sensor may be utilized to detect the container as filled with the initial sweat and to detect the container as refilled with the additional sweat. A coil located on a top section and a center section of the sweat rate monitor may be retracted to expand the container in order to allow room for the additional sweat in response to a detection of the volume of the initial sweat as forced out of the ejection port. The refill time may be recorded in response to detecting the container as filled with the additional sweat to determine the sweat rate from the start time, the refill time, and the volume of the initial sweat.

According to some examples a sweat rate monitor module to monitor a sweat rate of an area of a skin may be described. The sweat rate monitor module may include a container configured to capture an initial sweat that comes out of a surface of the skin. The sweat rate monitor may also include one or more analog inputs attached to the container, a support ring that encapsulates the container, and a processor. The processor may be configured to detect the container as filled with the initial sweat, actuate a pump attached to the support ring to compress the container in order to force a volume of the initial sweat in the container out of an ejection port of the container, and measure a start time of actuation of the pump and a refill time of the container with an additional sweat to determine the sweat rate.

According to other examples a surface of the container is sealed against the surface of the skin. The support ring is coated in a silicone-based material. The one or more analog inputs are attached to the container by an insertion of the one or more analog inputs into a depth of about 0.1 mm on to the surface of the container using a silicone material. The container is composed of a silicone-based material. The processor is further configured to force down a coil located on a top section and a center section of the container to force the volume of the initial sweat out of the container in response to detecting the container as filled with the initial sweat and retract the coil to expand the container in order to allow room for the additional sweat in response to a detection of the volume of the initial sweat as forced out of the ejection port. The coil is attached to the container with a gel adhesive. The sweat rate monitor module may further include a ring magnet attached to a top section of the container to actuate a coil to one or more of: compress the container and expand the container.

According to some examples, a system to monitor a sweat rate of an area of a skin may be described. The system may include a sweat rate monitor that includes a container, one or more continuity sensors attached to the container, a support ring that encapsulates the container, and an actuator to compress or expand the container. The container may be configured to capture an initial sweat that comes out of a surface of the skin. A processor may be communicatively coupled to the sweat rate monitor. The processor may be configured to detect the container as filled with the initial sweat, activate the actuator to compress the container to force a volume of the initial sweat in the container out of an ejection port of the container and to expand the container in order to allow room for additional sweat in response to a detection of the volume of the initial sweat as forced out of the ejection port, and determine the sweat rate based on a refill time detected in response to refilling of the container with the additional sweat.

In some examples, a sweat rate monitor module may be configured to monitor a sweat rate of an area of a skin. An example sweat rate monitor module may comprise a container configured to capture an initial sweat that emerges from the area of the skin after the module is placed against the area of the skin, one or more analog inputs attached to the container, and a support ring that at least helps encapsulates the container. In some examples, a monitor module may include a processor configured to (optionally) detect a surface of the container as sealed against the surface of the skin, detect when the container is filled with the initial sweat (for example using an electrical signal applied to and/or received from the one or more analog inputs), and actuate a pump attached to the support ring (e.g. by providing a pump actuation signal to the pump or associated control electronics, such as a switch circuit) to compress the container in order to force a volume of the initial sweat in the container out of an ejection port of the container. In some examples, the processor may be configured to determine a sweat rate, for example using a start time of actuation of the pump and a refill time of the container with an additional sweat. In some examples, a sweat rate may be determined from a measured interval between pump actuations and the volume ejected by the pump from the container. In some examples, a single sweat rate may be determined from a plurality of measurements. In some examples, the sweat rate may be determined as a dynamic parameter determined at intervals (e.g. at predetermined time intervals, or predetermined number of pump actuations). In some examples, a cumulative sweat volume may be determined, for example by summing the ejected volumes. In some examples, the processor may be located in the module proximate the container. In some examples, the processor may be located in a different location, while in electronic communication with the pump, analog inputs, and the like. In some examples, one or more processor functions may be achieved using an electronic device remote from the module an in communication with the module.

According to other examples, the processor may be further configured to determine the sweat rate based on an average of an initial fill time of the container with the initial sweat and the refill time. The processor may be further configured to analyze one or more outputs of the one or more continuity sensors and re-analyze the one or more outputs if at least one of the one or more outputs is below a sensor threshold value. The system may further comprise a display module configured to display the sweat rate upon receiving data from the processor. The processor may be further configured to record the sweat rate over a particular time period comprising refills of the container.

According to some examples a means to monitor a sweat rate of an area of a skin may be described. The means to monitor a sweat rage of an area of a skin may include a means to detect a sweat rate monitor as sealed against a surface of the skin, wherein the sweat rate monitor includes a container to capture an initial sweat that comes out of the surface of the skin, a means to detect the container as filled with the initial sweat, a means to actuate a pump of the sweat rate monitor to compress the container in order to force a volume of the initial sweat in the container out of an ejection port of the sweat rate monitor, and a means to measure a start time of actuation of the pump and a refill time of the container with an additional sweat to determine the sweat rate.

While various compositions, methods, systems, and devices are described in terms of "comprising" various components or steps (interpreted as meaning "including, but not limited to"), the compositions, methods, systems, and devices can also "consist essentially of" or "consist of" the various components and steps, and such terminology should be interpreted as defining essentially closed-member groups."

The foregoing detailed description has set forth various examples of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples may be implemented, individually and/or collectively, by a wide range of hardware, software, firmware, or virtually any combination thereof. In one example, several portions of the subject matter described herein may be implemented via Application Specific Integrated Circuits (ASICs), Field Programmable Gate Arrays (FPGAs), digital signal processors (DSPs), or other integrated formats. However, some aspects of the examples disclosed herein, in whole or in part, may be equivalently implemented in integrated circuits, as one or more computer programs running on one or more computers (for example, as one or more programs running on one or more computer systems), as one or more programs running on one or more processors (for example as one or more programs running on one or more microprocessors), as firmware, or as virtually any combination thereof, and that designing the circuitry and/or writing the code for the software and or firmware would be possible in light of this disclosure.

The present disclosure is not to be limited in terms of the particular examples described in this application, which are intended as illustrations of various aspects. Many modifications and variations can be made without departing from its spirit and scope Functionally equivalent methods and apparatuses within the scope of the disclosure, in addition to those enumerated herein, will be possible from the foregoing descriptions. Such modifications and variations are intended to fall within the scope of the appended claims. The present disclosure includes the terms of the appended claims, along with the full scope of equivalents to which such claims are entitled. It is to be understood that this disclosure is not limited to particular methods, systems, or components, which can, of course, vary. It is also to be understood that the terminology used herein is for the purpose of describing particular examples only, and is not intended to be limiting.

In addition, the mechanisms of the subject matter described herein are capable of being distributed as a program product in a variety of forms, and that an illustrative example of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (for example, a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that particular functionality is achieved. Hence, any two components herein combined to achieve a particular functionality may be seen as "associated with" each other such that the particular functionality is achieved, irrespective of architectures or intermediate components. Likewise, any two components so associated may also be viewed as being "operably connected", or "operably coupled", to each other to achieve the particular functionality, and any two components capable of being so associated may also be viewed as being "operably couplable", to each other to achieve the particular functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to examples containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

For any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and examples have been disclosed herein, other aspects and examples are possible. The various aspects and examples disclosed herein are for purposes of illustration and are not intended to be limiting, with the true scope and spirit being indicated by the following claims.

What is claimed is:

1. A sweat rate monitor module to monitor a sweat rate of an area of a skin, the sweat rate monitor module comprising:
   a container configured to capture an initial sweat that comes out of a surface of the skin;
   one or more analog inputs attached to the container;
   a support ring that encapsulates the container; and
   a processor configured to perform or cause to be performed:
      detect the container as filled with the initial sweat;
      actuate a pump attached to the support ring to compress the container in order to force a volume of the initial sweat in the container out of an ejection port of the container; and
      measure a start time of the actuation of the pump and a refill time of the container with an additional sweat to determine the sweat rate.

2. The sweat rate monitor module of claim 1, wherein a surface of the container is configured to be sealed against the surface of the skin.

3. The sweat rate monitor module of claim 1, wherein the support ring is coated with a silicone-based material.

4. The sweat rate monitor module of claim 1, wherein the one or more analog inputs are attached by a silicone material to the container by insertion of the one or more analog inputs into a depth of about 0.1 mm into a surface of the container.

5. The sweat rate monitor module of claim 1, wherein the container comprises a silicone-based material.

6. The sweat rate monitor module of claim 1, wherein the processor is further configured to perform or cause to be performed:
   force down a coil located on a top section and a center section of the container to force the volume of the initial sweat out of the container, in response to the detection of the container as filled with the initial sweat; and
   retract the coil to expand the container in order to allow room for the additional sweat, in response to a detection of the volume of the initial sweat as forced out of the ejection port of the container.

7. The sweat rate monitor module of claim 6, wherein the coil is attached to the container with a gel adhesive.

8. The sweat rate monitor module of claim 1, further comprising a ring magnet attached to a top section of the container to actuate a coil to one or more of compress the container and expand the container.

* * * * *